(12) United States Patent
Ribitsch et al.

(10) Patent No.: US 9,791,377 B2
(45) Date of Patent: Oct. 17, 2017

(54) OPTOCHEMICAL SENSOR

(71) Applicant: TecSense Gmbh, Grambach (AT)

(72) Inventors: Volker Ribitsch, Graz (AT); Johannes Krottmaier, Hart bei Graz (AT)

(73) Assignee: TECSENSE GMBH, Grambach (AT)

( * ) Notice: Subject to any disclaimer, the term of this patent is extended or adjusted under 35 U.S.C. 154(b) by 52 days.

(21) Appl. No.: 15/031,866

(22) PCT Filed: Oct. 15, 2014

(86) PCT No.: PCT/AT2014/000184
§ 371 (c)(1),
(2) Date: Apr. 25, 2016

(87) PCT Pub. No.: WO2015/058221
PCT Pub. Date: Apr. 30, 2015

(65) Prior Publication Data
US 2016/0266044 A1   Sep. 15, 2016

(30) Foreign Application Priority Data

Oct. 23, 2013   (AT) ................. GM345/2013

(51) Int. Cl.
*G01N 21/77*   (2006.01)
*G01J 3/02*   (2006.01)
(Continued)

(52) U.S. Cl.
CPC ............ *G01N 21/77* (2013.01); *G01J 3/0202* (2013.01); *G01J 3/0272* (2013.01); *G01J 3/0291* (2013.01); *G01J 3/4406* (2013.01); *G01N 21/643* (2013.01); *G01N 21/645* (2013.01); *G01N 21/6428* (2013.01); *G01N 21/7703* (2013.01); *G01N 2021/6419* (2013.01); *G01N 2021/6432* (2013.01); *G01N 2021/6441* (2013.01);
(Continued)

(58) Field of Classification Search
None
See application file for complete search history.

(56) References Cited

U.S. PATENT DOCUMENTS 6,448,064 B1   9/2002   Vo-Dinh et al.
2002/0164813 A1   11/2002   Colvin, Jr. et al.
(Continued)

OTHER PUBLICATIONS

International Search Report, dated Jun. 26, 2015 (3 pages).

*Primary Examiner* — Edwin Gunberg
(74) *Attorney, Agent, or Firm* — Jacobson Holman, PLLC.

(57) ABSTRACT

An optochemical sensor comprises a measuring element excitable by the light of an excitation light source and in contact with a medium to be measured, and a measuring arrangement including at least one excitation light source and a detector as well as a hood separating the measuring arrangement from the measuring element, wherein the excitation light source and the detector are fixed to a base plate arranged in parallel with the measuring element, the hood, the excitation light source and the detector are separated from one another by at least a portion of the material thickness of the hood, and light from the excitation light source through an optical waveguide impinges on the measuring element at such an angle that fluorescence light emitted by the measuring element impinges perpendicularly on the detector.

13 Claims, 1 Drawing Sheet

(51) Int. Cl.
*G01J 3/44* (2006.01)
*G01N 21/64* (2006.01)

(52) U.S. Cl.
CPC ............ *G01N 2021/6484* (2013.01); *G01N 2021/7786* (2013.01); *G01N 2021/7793* (2013.01); *G01N 2021/7796* (2013.01); *G01N 2201/064* (2013.01)

(56) References Cited

U.S. PATENT DOCUMENTS

| | | |
|---|---|---|
| 2005/0237518 A1 | 10/2005 | Colvin, Jr. et al. |
| 2006/0197960 A1 | 9/2006 | Bazylenko |
| 2007/0102654 A1* | 5/2007 | Schoo .................. G01N 21/274 250/576 |
| 2008/0180673 A1 | 7/2008 | Sampas et al. |

* cited by examiner

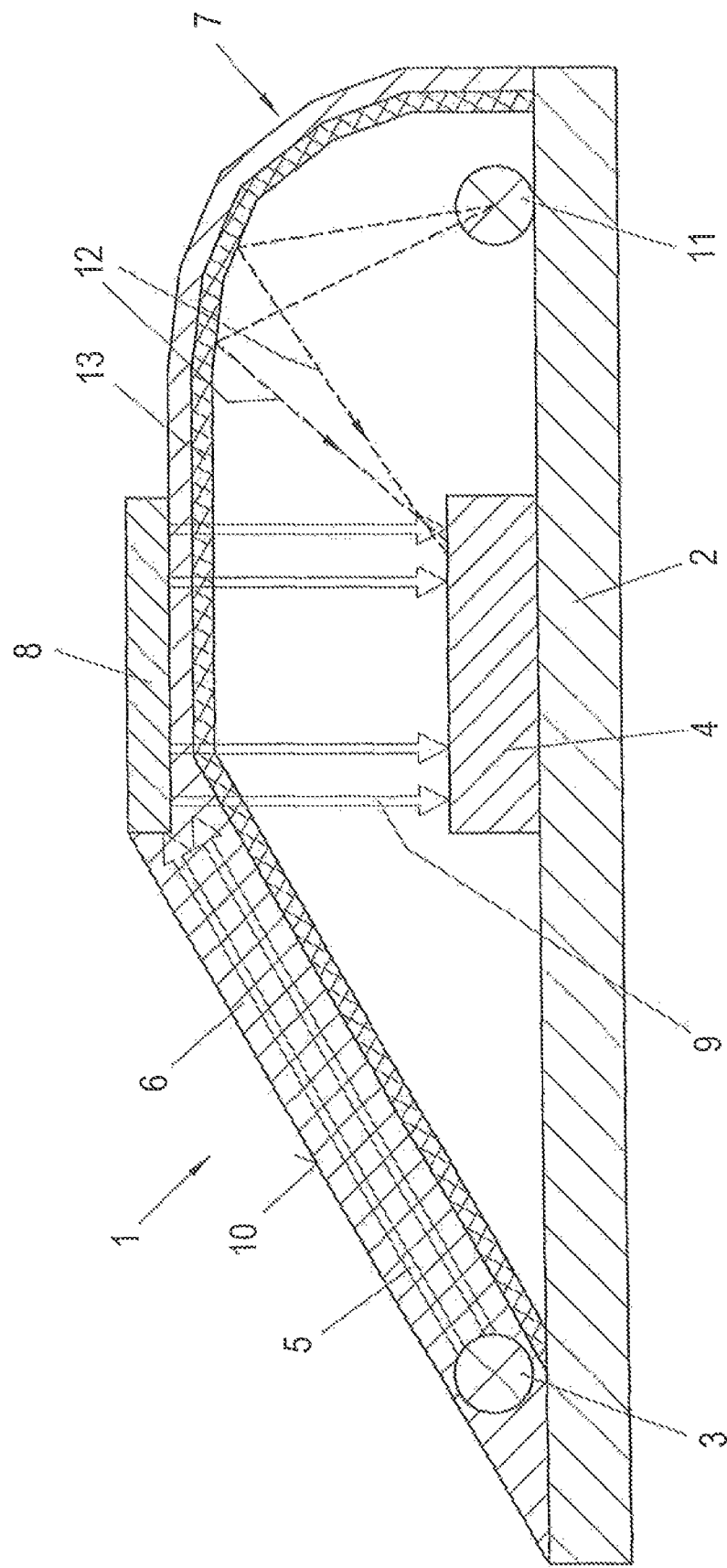

OPTOCHEMICAL SENSOR

The present invention relates to an optochemical sensor comprising a measuring element excitable by the light of an excitation light source and in contact with a medium to be measured, and a measuring arrangement including at least one excitation light source and a detector as well as a hood separating the measuring arrangement from the measuring element.

BACKGROUND OF THE INVENTION

Optochemical sensors have been used to an increasing extent for measuring a great variety of fluids such as gases, liquids or even, mixtures thereof, both in the medical, biological or biochemical field and in the food and other laboratory or industrial sectors in order to enable the rapid and reliable detection of the presence or absence of specific substances. Gases whose presence or absence is determined by such sensors, for instance, include oxygen, $CO_2$, but also, for instance, ozone or ammonia. Furthermore, such sensors have allowed, for instance in the medical field by measuring biomolecules or pathogenic substances, to draw conclusions on, for instance, wound healing, wound contamination, the presence or absence of certain pathogens or the like, in that they are, for instance, employed for measuring pH values, which can be used for conclusions on such processes.

The operating principle of optochemical sensors basically relies on the interaction of a substance excitable by light with the analyte to be measured, wherein the excitable substance is excited by light of a specific, suitable wavelength and the molecules, after having been excited, emit the absorbed energy in the form of fluorescence light when returning into their original state, which fluorescence light is extinguished by interactions with the analyte. In order enable the detection of such an extinction of the fluorescence light, it is necessary, on the one hand, for the fluorescence light to have sufficient intensity and, on the other hand, for the non-extinguished fluorescence light to be reflected onto a detector, which will detect the presence or absence of an analyte based on the measurement of the intensity of the fluorescence light.

The substance to be excited by the radiated light is usually a so-called fluorophore, which, during the use of such an optochemical sensor, is either in direct contact with the substance to be measured or is protected from noxious environmental influences by a cover permeable to the substance to be detected. During the operation of such a sensor, the fluorophore is usually radiated from the side facing away from the substance to be measured, excited, and the non-extinguished fluorescence light is absorbed or captured on a suitable detector also facing away from the sample to be measured and/or provided in a housing protected from the sample to be measured, optionally amplified, and subsequently measured.

In particular when using such sensors in the medical or biological field, it is essential that the sensors are dimensioned as small as possible and that they can preferably be used in so-called micro total analysis systems (TAS).

Thus, in particular the question of the size of such sensors has become more and more important, since recently not only the range of application of such sensors has grown tremendously but also attempts have, for instance, been made to enable without special expenditure in small-structured, e.g. medical, equipment in addition to other required activities such as, e.g. in connection with catheters, the introduction of tools into wounds, or of optical devices for in-situ observation or the like, the direct detection of, for instance, the presence or absence of analytes to be assayed; it has turned out to be especially essential and important that such sensors can be miniaturized or optionally be built so small as to be integratable into microchips or mountable on printed circuit boards, which cannot be achieved by systems available at present.

The integration of such optochemical sensors in chips involves the recurring problem that the sensors require a separation of the fluorescence light from the excitation light by means of a spectrometer or by using optical filters, which has turned out to be unsatisfactory, since the intensity of the excitation light is usually significantly higher than the intensity of the generated fluorescence light, which constitutes a problem for the measuring accuracy, in particular in miniaturized systems, since stray light might disturb or falsify measurements.

US 2008/0180673 A1 describes a test system including an optical medium, a binding agent and a light, detector. The optical medium provides a light path and the binding agent is positioned so as to hold a target complex in an evanescing field formed by the propagation of light along the light path. Due to the interaction of the complex with the evanescing field, light is emitted, which is impinges on a detector positioned for the detection of the light.

From U.S. Pat. No. 6,448,064 B1, a miniaturized DNA biosensor can be taken, which is designed to detect specific molecular targets like nucleic acids. The miniaturized biosensor is a chip comprising multiple biological sensing elements, excitation microlasers, a sampling waveguide equipped with optical detectors, integrated electro-optics, and a biotelemetric radiofrequency signal generator. Such a device is suitable for gene analysis.

From US 2005/0237518 A1, an optical sensor device for determining the presence or concentration of an analyte can be taken, coprising a waveguide disposed over a light source and a light detector mounted on a surface of a substrate and separated from the light source, wherein the waveguide has a thickness corresponding to a far-field emission point of the light source. An analyte indicator matrix is, moreover, disposed on the outer surface of the waveguide.

From US 2002/016413 A1, an electro-optical sensing device for detecting the present or concentration of an analyte in a liquid or gaseous medium can be taken, which device included a pair of indicator elements positioned to receive radiation from a radiation source transmit said radiation to a pair of photosensitive elements.

US 2006/0197960 A1 finally discloses a biochip for testing biological substances, comprising a plurality of binding sites, optical means for determining a specific binding event at each binding site, wherein the plurality of binding sites and the means for determining are integrated in a single chip which is electrically powered and produces signals in response to the binding events at each binding site.

BRIEF SUMMARY OF THE INVENTION

The present invention is therefore based on the object to provide an optochemical sensor that is tight and insensitive to possible interferences, on the one hand, and to miniaturize the sensor design to such an extent that it can be integrated in small- and smallest-structured devices like chips or printed circuit boards, on the other hand. To solve this object, the sensor according to the invention is essentially characterized in that the excitation light source and the detector are fixed to a base plate arranged in parallel with the measuring element, that the excitation light source and the detector are separated from each other by at least a portion of the material thickness of the hood, that light from the excitation light source through an optical waveguide impinges on the measuring element at such an angle that fluorescence light emitted by the measuring element impinges perpendicularly on the detector, that a reference light source is disposed on the base plate at a distance from the excitation light source and the detector, that the excitation light source, the detector and the reference light source are arranged on one axis, and that the hood is detachably fixed to the base plate. In that the configuration is devised such that the excitation light source and the detector are fixed to a base plate arranged in parallel with the measuring element, the structural height of the optochemical sensor can be reduced as much as possible and, in that, moreover, the hood separates the excitation light source from the detector by at least a portion of its material thickness, not only a geometric separation of the element is provided, but it is also ensured that, irrespective of the intensity of the excitation light, any interference with the same will be safely prevented, thus enhancing the measuring accuracy of the system over conventional systems despite the small-structured arrangement of the elements of the sensor. In that, moreover, light from the excitation light source through an optical waveguide impinges on the measuring element at such an angle that the fluorescence light emitted by the measuring element impinges perpendicularly on the detector, it is ensured that, on the one hand, the structural height of the overall device is further reduced and, on the other hand, the light output of the fluorescence light is maximized and the measuring accuracy is thus increased. In that the sensor is designed such that a reference light source is disposed on the base plate at a distance from the excitation light source and the detector, and that the excitation light source, the detector and the reference light source are arranged on one axis, it has become possible to measure both excitation light and reference light by one and the same detector, which enables the measurement of, for instance, changes in the reflection intensity so as to further increase the measuring accuracy of the device as opposed to conventional devices. In that, moreover, the excitation light source, the detector and the reference light source are arranged on one axis, it is ensured that no interferences will occur between the excitation light source and the reference light source, since these two light sources are spatially separated from each other, in particular by the detector installed therebetween and at least a portion of the hood. Particularly simple handling of the optochemical sensor will be ensured in that the hood is detachably fixed to the base plate. Such a configuration will, for instance, enable the problem-free exchange of individual elements fixed to the base plate, e.g. the detector or the hood itself, so as to extend the overall service life of the sensor.

According to a further development of the invention, the optochemical sensor is configured such that the excitation light source is embedded in the material thickness of the hood. With such a configuration, any unintentional stray light from the excitation light source in the direction of the detector or into the interior of the optochemical sensor will be safely prevented, and that part of the hood in which the excitation light source is integrated can, for instance, be formed with a larger material thickness than the remaining hood, which comprises reflectors so as to reflect, for instance, possibly present stray and, moreover, provide an effective separation of the excitation light source from the detector.

In that, as in correspondence with a further development of the invention, the sensor is configured such that a portion of the hood located between the excitation light source and the measuring element comprises a smoothened surface and is designed as an optical waveguide, it has become possible to use a portion of the hood directly as an optical waveguide such that the optochemical sensor can not only be simplified in terms of hardware but also further miniaturized. In addition, the generation of any stray light whatsoever will be effectively avoided by such a configuration.

In doing so, it has become possible, as in correspondence with a further development of the invention, to configure the sensor such that the measuring element is directly applied to an end portion of the fiber-optic elements forming the optical waveguide, and that the hood is at least partially comprised of glass and/or of polycarbonate containing glass fibers. With such a configuration the sensor can be applied directly to the end regions of fiber-optic elements forming the optical waveguide, which, for instance in a multi-purpose element such as a catheter, will, for instance, enable some of the fiber-optic cables to be used as optical waveguides for the optochemical sensor besides the elements required for the operation of the same. In that the hood is, moreover, partially comprised of glass or of polycarbonate containing glass fibers, such a configuration enables the entire sensor to be formed in the end region of the fiber-optic cables so as to reach only a minimal structural, enlargement of a fiber-optic bundle formed, for instance, in a catheter for surgical or microsurgical application.

In that, as in correspondence with a further development of the invention, the optochemical sensor is further developed such that an inner surface of the hood is designed as, or comprises, a unidirectional radiation barrier, it is ensured that reference light will not accidentally emerge from the optochemical sensor and enter the fluid to be detected. Moreover, such a configuration ensures that light from the detection light source will not negatively influence any measurement made by the measuring element and the detector, but that the light of the reference light source will be directly and completely reflected onto the detector and hence be available as a comparative signal for said measurement.

According to a further development of the invention, the optochemical sensor is designed such that the inner surface of the hood is mirrored or comprises a vaporized layer totally reflecting the light from the reference light source. By providing a mirror coating on the inner surface or polished surface of the hood, the total reflection of the light of the reference light source will be ensured in the same manner as by a layer vaporized on the inner surface of the hood for totally reflecting light from the reference source. Such a configuration not only enables the total reflection of the light of the reference light source onto the detector but also ensures that an increase in the structural dimensions of the entire optochemical sensor will be prevented such that the sensor per se will remain small-structured and integrable in small-structured electric or electronic devices such as microsurgical elements and probes catheters and the like.

In order to simultaneously ensure that light will not be unintentionally reflected by the measuring element or fluorophore, or partially given off or reflected into the sample to be assayed, the optochemical sensor is further developed to the effect that the hood, in the region of the measuring element, is formed with a roughened outer surface permeable to fluorescence light. Such a configuration will ensure, merely by choosing the smoothness of the outer surface of the hood, that certain areas of the latter will be permeable to light of certain wavelengths, or will in any case reflect extraneous light, so as to enable the structural dimensions of the entire sensor to be further reduced. Besides, a roughened surface in the region of the measuring element will provide a stronger adherence or connection to the hood of the polymers contained in the measuring element so as to markedly enhance the durability of the sensor.

In order to safely prevent any inadvertent detachment of the measuring element from the hood, the invention, in addition to the above-identified measures, is further developed to the effect that the measuring element is comprised of base material capable of being cross-linked with a material of the hood and containing a fluorophore, in particular in the dissolved state. Materials ensuring cross-linking of the measuring element with the hood include base materials consisting of silicic acid ethyl ester (PEOS) and/or tetraethyl orthosilicate (TEOS). As in accordance with the general prior art, a fluorophore is admixed in a defined amount to such a base material of the measuring element in order to provide the respective, desired fluorescence properties.

For a particularly small-structured device, the optochemical sensor, as in correspondence with a further development of the invention, can be devised such that the measuring element is designed as a divided measuring element comprising two fluorophores optionally differing from each other. Such a configuration enables the measurement of two different analytes at the same time so as to rapidly and reliably provide several statements on samples to be assayed without enlarging the sensor as a whole.

In this respect, the device can be further developed to the effect that the divided measuring element is excitable by two different excitation light sources. By providing two different excitation light sources, it has become possible to emit two different excitation light wavelengths, and hence also receive two different fluorescence light wavelengths, such that even simultaneously performed measurements of several analytes can be clearly distinguished from one another and detected free of interference. In this respect, it is, of course, also possible to provide two mutually separated detectors.

In order to be able to simultaneously measure a plurality of analytes without mutual interference, the invention is further developed to the effect that a plurality of identical or different optochemical sensors are arranged on a base plate so as to enable the measurement of different analytes at the same time.

Such an arrangement will, in particular, be useful if, as in correspondence with a further development of the invention, the base plate is comprised of a printed circuit board, whereby a single electronic unit will enable the measurement of a plurality of analytes at the same time.

BRIEF DESCRIPTION OF THE DRAWING

In the following, the invention will be explained in more detail by way of an exemplary embodiment illustrated in the drawing; therein, FIG. 1 illustrates a section through a schematic arrangement of an optochemical sensor according to the invention.

DETAILED DESCRIPTION OF THE INVENTION

In FIG. 1, an optochemical sensor is denoted by 1, in which an excitation light source 3 and a detector 4 are fixed to a base plate 2. Light from the excitation light source 3, which is schematically indicated by 5, is radiated to a measuring element 8 through a portion 6 of a hood 7, which portion is designed as a light guide. The measuring element 8, which, in this case, is comprised of fluorophore dissolved or dispersed in a polymer base material, is, in particular, cross-linked with a surface roughened in the region of the measuring element 8, of the hood 7.

The excitation light source 5 excites the molecules of the fluorophore contained in the measuring element to emit fluorescence light, which fluorescence light contacts the molecules of a sample to be assayed and is optionally extinguished by said molecules. Non-extinguished light is reflected on the detector 4, and from measuring the intensity of the reflected radiation 9, which may optionally even be increased, the presence and absence of an analyte in a sample to be assayed can be concluded.

In the configuration according to FIG. 1, the excitation light source 3 is embedded in a portion of increased thickness 6 of the hood 7, and the outer surface 10 of the portion of increased thickness 6 of the hood 7 is highly mirrored and, in particular, extremely smooth such that the portion 6 of the hood 7 can itself serve as an optical waveguide. According to a variant, a separate optical waveguide is provided in the interior of said portion 6 of the hood 7, without however changing the overall structure of the optochemical sensor 1.

In the illustration according to FIG. 1, a reference light source 11 is, moreover, disposed on the base plate 2, the light of which reference light source is reflected onto the detector 4, on the inner side of the hood 7, as is schematically indicated by reference numeral 12. In the illustration according to FIG. 1, a layer 13 designed as a unidirectional radiation barrier is, moreover, vaporized on the inner side of the hood 7. Said unidirectional radiation barrier 13 is comprised of a layer that is formed to be extremely smooth on the inner side, in particular vaporized on the inner surface of the hood 7, so as to be totally reflective for the light 12 of the reference light source 11. The reference light 12 thus will not reach the outside of the optochemical sensor 1 and, therefore, will not interfere with any substance measurement. The same applies to the excitation light 5 of the excitation light source 3, which is likewise unable to emit stray light to the outside or into the interior of the optochemical sensor, so that measurements free of stray light influences can be performed. This is of particular importance because the excitation light 5 and the reference light 12 usually have higher intensities than the fluorescence light of the fluorophore such that even small disturbances might strongly falsify measurements or render them inaccurate.

The invention claimed is:

1. An optochemical sensor comprising a measuring element excitable by the light of an excitation light source and in contact with a medium to be measured, and a measuring arrangement including at least one excitation light source and a detector as well as a hood separating the measuring arrangement from the measuring element, wherein the excitation light source and the detector are fixed to a base plate arranged in parallel with the measuring element, that the excitation light source and the detector are separated from each other by at least a portion of the material thickness of the hood, that light from the excitation light source through an optical waveguide impinges on the measuring element at such an angle that fluorescence light emitted by the measuring element impinges perpendicularly on the detector, that a reference light source is disposed on the base plate at a distance from the excitation light source and the detector, that the excitation light source, the detector and the reference light source are arranged on one axis, and that the hood is detachably fixed to the base plate.

2. The optochemical sensor according to claim 1, wherein the excitation light source is embedded in the material thickness of the hood.

3. The optochemical sensor according to claim 1, wherein a portion of the hood located between the excitation light source and the measuring element comprises a smoothened surface and is designed as an optical waveguide.

4. The optochemical sensor according to claim 1, wherein the measuring element is directly applied to an end portion of the fiber-optic elements forming the optical waveguide, and that the hood is at least partially comprised of glass and/or of polycarbonate containing glass fibers.

5. The optochemical sensor according to claim 1, wherein an inner surface of the hood is designed as, or comprises, a unidirectional radiation barrier.

6. The optochemical sensor according to claim 5, wherein the inner surface of the hood is mirrored or comprises a vaporized layer totally reflecting the light from the reference light source.

7. The optochemical sensor according to claim 1, wherein the hood, in the region of the measuring element, is formed with a roughened outer surface permeable to fluorescence light.

8. The optochemical sensor according to claim 1, wherein the measuring element is comprised of a base material capable of being cross-linked with a material of the hood and containing a fluorophore, in particular in the dissolved state.

9. The optochemical sensor according to claim 1, wherein the base material of the measuring element is selected from silicic acid ethyl ester or tetraethyl orthosilicate.

10. The optochemical sensor according to claim 1, wherein the measuring element is designed as a divided measuring element comprising two fluorophores optionally differing from each other.

11. The optochemical sensor according to claim 10, wherein the divided measuring element is excitable by two different excitation light sources.

12. The optochemical sensor according to claim 1, wherein a plurality of identical or different optochemical sensors are arranged on a base plate.

13. The optochemical sensor according to claim 1, wherein the base plate is comprised of a printed circuit board.

\* \* \* \* \*